United States Patent
Rittig et al.

(10) Patent No.: US 10,337,144 B2
(45) Date of Patent: *Jul. 2, 2019

(54) METHOD FOR PROCESSING CELLULOSE-CONTAINING BIOMASS

(71) Applicant: BASF SE, Ludwigshafen (DE)

(72) Inventors: Frank Rittig, Osthofen (DE); Stefan Koch, Mainz (DE); Alois Kindler, Gruenstadt (DE); Michael Koch, Speyer (DE); Ferdinand Leifeld, Ludwigshafen (DE); Vaidotas Navickas, Mannheim (DE); Markus Gruen, Birkenheide (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/552,522

(22) PCT Filed: Feb. 18, 2016

(86) PCT No.: PCT/EP2016/053418
§ 371 (c)(1),
(2) Date: Aug. 22, 2017

(87) PCT Pub. No.: WO2016/135031
PCT Pub. Date: Sep. 1, 2016

(65) Prior Publication Data
US 2018/0051414 A1 Feb. 22, 2018

(30) Foreign Application Priority Data
Feb. 23, 2015 (EP) ..................... 15156148

(51) Int. Cl.
| | |
|---|---|
| *C12P 19/02* | (2006.01) |
| *C08H 8/00* | (2010.01) |
| *C12N 1/22* | (2006.01) |
| *D21C 1/04* | (2006.01) |
| *C08B 1/00* | (2006.01) |
| *C08B 15/02* | (2006.01) |
| *C12P 19/14* | (2006.01) |

(52) U.S. Cl.
CPC ............... *D21C 1/04* (2013.01); *C08B 1/003* (2013.01); *C08B 15/02* (2013.01); *C08H 8/00* (2013.01); *C12P 19/02* (2013.01); *C12P 19/14* (2013.01); *Y02E 50/16* (2013.01)

(58) Field of Classification Search
CPC ......... C12P 19/02; C08B 1/003; C08B 15/02; C12K 1/02; C08H 8/00
USPC ............................................ 435/99, 97, 146
See application file for complete search history.

(56) References Cited

U.S. PATENT DOCUMENTS

| | | | |
|---|---|---|---|
| 6,963,014 | B1 | 11/2005 | Zeller et al. |
| 7,419,568 | B2 | 9/2008 | Hamed et al. |
| 2003/0230391 | A1 | 12/2003 | Hamed et al. |
| 2004/0084159 | A1 | 5/2004 | Hamed et al. |
| 2005/0256470 | A1 | 11/2005 | Hamed et al. |
| 2005/0263258 | A1 | 12/2005 | Hamed et al. |
| 2012/0029247 | A1 | 2/2012 | Holbrey et al. |
| 2015/0051385 | A1 | 2/2015 | Binder |

FOREIGN PATENT DOCUMENTS

| | | |
|---|---|---|
| EP | 0 472 474 A1 | 2/1992 |
| EP | 2 033 974 A1 | 3/2009 |
| WO | WO 2004/081185 A2 | 9/2004 |
| WO | WO 2008/134037 A1 | 11/2008 |
| WO | WO 2013/162881 A1 | 10/2013 |
| WO | WO 2015/049345 A1 | 4/2015 |

OTHER PUBLICATIONS

International Search Report and Written Opinion dated May 2, 2016 in PCT/EP2016/053418.
Extended European Search Report dated Jul. 20, 2015 in Patent Application No. 15156148.7.
Hairong Zhang, et al., "Acid-Catalyzed Liquefaction of Bagasse in the Presence of Polyhydric Alcohol" Applied Biochemistry Biotechnology, vol. 170, 2013, XP055196984A, pp. 1780-1791.
Hong-Yuan Wang, et al., "Effects of rhamnolipid on the cellulose and xylanase in hydrolysis of wheat straw" Bioresource Technology, vol. 102, 2011, XP028480902A, pp. 6515-6521.
Mareike Monschein, et al., "Dissecting the effect of chemical additives on the enzymatic hydrolysis of pretreated wheat straw" Bioresource Technology, vol. 169, 2014, XP055196639A, pp. 713-722.

*Primary Examiner* — Robert B Mondesi
*Assistant Examiner* — Mohammad Y Meah
(74) *Attorney, Agent, or Firm* — Oblon, McClelland, Maier & Neustadt, L.L.P.

(57) ABSTRACT

Described is a method for processing cellulose-containing biomass with sulfuric acid and certain additives, especially for the pretreatment of cellulose-containing biomass prior to saccharification.

18 Claims, No Drawings

METHOD FOR PROCESSING CELLULOSE-CONTAINING BIOMASS

Sugars generated from cellulose-containing biomass may be used as a feedstock for production of fuels, plastics, and other products. Due to the finite nature and instability of fossil feedstock supply and for environmental reasons, replacement of fossil feedstock by non-fossil feedstock, i.e. feedstock obtained from renewable resources, becomes more and more important. One potential source of such non-fossil feedstock is cellulose-containing biomass, which can be processed by enzymatic saccharification of cellulose to glucose which can be further processed into a plurality of products either chemically or by fermentation. For instance, by fermentation of the obtained glucose, ethanol (sometimes referred to as bio-ethanol) is obtainable which can be used as fuel for internal combustion engines, e.g. for cars.

In order to facilitate enzymatic saccharification, cellulose-containing biomass is usually subjected to a pretreatment in order to increase the accessibility of the cellulose biomass by degradation or decomposition of hemicellulose and/or lignin present in the cellulose-containing biomass. Several pretreatment processes are known in the art.

WO 2008/134037 discloses a method for digesting a lignocellulosic biomass, comprising treating a lignocellulosic biomass with a surfactant and optionally an acid (e.g. sulfuric acid) and incubating the surfactant treated lignocellulosic biomass with an enzyme. Preferred surfactants are chosen from the group consisting of Tween-80, Tween-20, PEG (molar mass not specified), DDBSA, glucopone/215, glucopone/225 and glucopone/625.

WO 2004/081185 discloses a method for hydrolyzing lignocellulose, comprising contacting said lignocellulose with at least one chemical under moderate conditions to generate a treated lignocellulose, and contacting said treated lignocellulose with at least one enzyme capable of hydrolyzing lignocellulose, wherein said chemical is selected from the group consisting of oxidizing agents, denaturants, detergents, organic solvents, bases, and combinations thereof. In this regard, by "detergent" is intended a compound that can form micelles to sequester oils. Said detergents including anionic, cationic, and neutral detergents, including, but not limited to, Nonidet (N) P-40, sodium dodecyl sulfate (SDS), sulfobetaine, noctylglucoside, deoxycholate, Triton X-100, and Tween 20.

In the publication Bioresource Technology 169 (2014) 713-722 the ability of additives selected from the group consisting of polyethylene glycol PEG 8000, (polyethylene glycol having a molar mass of approximately 8000 g/mol), PEG 2000 (polyethylene glycol having a molar mass of approximately 2000 g/mol), Triton-X, Tween 20, Tween-80, cetyltrimethylammonium bromide (CTAB) and urea to increase the enzymatic hydrolysis of thermo-acidically pretreated wheat straw by *Trichoderma reesei* cellulase at 50° C. is studied. Herein, the additive is added to a suspension of thermo-acidically pretreated wheat straw. Presence of an additive during the thermo-acidical pretreatment is not disclosed.

Related art is also Hong-Yuan Wang et al., Bioresource Technology vol. 102 no. 11, 24 Feb. 2011, pages 6515-6521, EP 0 472 474 A1, Hairong Zhang et al., Applied Biochemistry and Biotechnology vol. 170, no. 7, 1 Aug. 2013, pages 1780-1791; WO 2013/162881 A1, U.S. Pat. No. 7,419,568 B2, EP 2 033 974 A1 and WO 2015/049345 A1.

WO 2008/134037 and WO 2004/081185 broadly disclose generic classes of additives for the pretreatment of cellulose-containing biomass prior to saccharification. However it has been found that the chemical structure as well as the molecule size of such additive has a strong influence on the effect of said additive. Surprisingly it has been found that the use of compounds of formula (I) as defined hereinbelow for processing cellulose-containing biomass, especially for the pretreatment of cellulose-containing biomass prior to saccharification, has an advantageous effect on the yield of glucose obtainable by enzymatic saccharification of the treated cellulose containing biomass.

These and other objects are achieved by the method for processing cellulose-containing biomass according to the present invention. Said method for processing cellulose-containing biomass comprises the step of subjecting a treatment mixture comprising said cellulose-containing biomass, water and sulfuric acid to a temperature in the range of from 100° C. to 220° C. at a pressure in the range of from 100 to 4000 kPa wherein the pressure is selected so that at least a part of the water is in the liquid state to generate a treated cellulose-containing biomass, wherein said treatment mixture further comprises one or more compounds of formula (I)

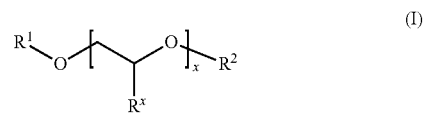

wherein in formula (I)

$R^1$ is selected from the group consisting of hydrogen and methyl $R^2$ is selected from the group consisting of branched and non-branched alkyl having 9 to 22 carbon atoms, each $R^x$ in any of said x groups (II)

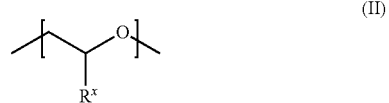

is independently of the meaning of $R^x$ in the other groups (II) selected from the group consisting of hydrogen and methyl, x is an integer from 3 to 40.

The step of subjecting a treatment mixture as defined above comprising said cellulose-containing biomass, water, sulfuric acid and one or more compounds of formula (I) to a temperature in the range of from 100° C. to 220° C. at a pressure in the range of from 100 kPa to 4000 kPa wherein the pressure is selected so that at least a part of the water is in the liquid state facilitates saccharification, either enzymatic or chemical saccharification, of the obtained treated cellulose-containing biomass. Therefore, in a preferred method according to the present invention, said step provides a useful pretreatment of cellulose-containing biomass for saccharification, either enzymatic or chemical saccharification, or for the production of dissolving pulp.

The treated cellulose-containing biomass typically comprises cellulose, hemicellulose and lignin as major components. In contrast to the cellulose-containing biomass before processing, in the treated cellulose-containing biomass the content of hemicellulose and/or lignin is typically decreased due to decomposition to xylose and other degradation products which may include minor amounts of glucose. Accordingly, in a preferred method of the present invention, the composition of the treatment mixture and the temperature and pressure to which said treatment mixture is subjected are selected such as to decrease the amount of hemicellulose and/or lignin in the cellulose-containing biomass.

Without wishing to be bound to any specific theory, it is presently assumed that the compounds of formula (I) bind to lignin constituents of the cellulose-containing biomass thus preventing lignin from inhibiting the activity of the enzymes in enzymatic saccharification of the treated cellulose-containing biomass. Furthermore the compounds of formula (I) may facilitate swelling of the cellulose-containing biomass, resulting in stabilization of an open structure of the cellulose-containing biomass which improves the access of sulfuric acid as well as of enzymes for subsequent enzymatic saccharification. More specifically the molecules of the compounds of formula (I) may fill voids in the treated biomass which are formed due to decomposition of hemicellulose and/or lignin, thus avoiding densification and collapsing of the treated cellulose-containing biomass so that in the enzymatic saccharification access of enzymes is facilitated.

A further aspect of the present invention relates to the use of a compound of formula (I) as defined above for processing cellulose-containing biomass, especially for the pretreatment of cellulose-containing biomass prior to saccharification.

Treatment Mixture

The treatment mixture comprises a solid phase comprising cellulose containing biomass and a liquid aqueous phase comprising water, sulfuric acid and one or more compounds of formula (I).

Cellulose-containing biomass which is suitable for processing by the method of the present invention may be selected from the group consisting of plant biomass, agricultural wastes, forestry residues, sugar processing residues, paper waste and blends thereof. For economical and ecological reasons, cellulose containing biomass in the form of wastes and residues is especially preferably. Beside cellulose, cellulose-containing biomass typically comprises lignin and/or hemicellulose.

Preferably said treatment mixture comprises 3 wt.-% to 75 wt.-%, more preferably 8 wt.-% to 70 wt.-%, further preferably 15 wt.-% to 60 wt.-%, most preferably 25 wt.-% to 50 wt.-%, particularly preferably 30 wt.-% to 45 wt.-% of cellulose containing biomass, in each case based on the total weight of said treatment mixture. With a lower concentration of cellulose-containing biomass in the treatment mixture, the method becomes inefficient, because a very large volume of treatment mixture is handled for obtaining a small amount of treated cellulose-containing biomass. With a higher concentration of biomass in the treatment mixture, there is an issue that not all of the cellulose-containing biomass is in contact with the sulfuric acid and the one or more compounds of formula (I) as defined above.

Preferably the concentration of sulfuric acid in said treatment mixture is in the range of from 0.1 wt.-% to 25 wt.-%, more preferably 0.5 wt.-% to 10 wt.-%, most preferably 1 wt.-% to 5 wt.-% in each case based on the total weight of the cellulose-containing biomass present in the treatment mixture.

At a concentration below 0.1 wt.-% based on the total weight of the cellulose-containing biomass present in the treatment mixture, the amount of sulfuric acid in the treatment mixture is generally too low so that the sulfuric acid has no significant effect on the yield of glucose in subsequent saccharification. On the other hand, the higher the concentration of sulfuric acid in the treatment mixture, the higher is the amount of undesirable by-products. Sulfuric acid may act as an oxidation agent and/or as a dehydrating agent, therefore undesired by-products may be formed by coking and/or sulfatization of biomass constituents. Formation of such by-products in turn results in reduction of the amount of material available for saccharification, contamination of the reaction mixture, deactivation of enzymes used for saccharification, contamination of the reaction equipment (i.e. by formation of insoluble deposits) and difficulties in separating the phases of the treatment mixture.

For this reason, it is preferred that the concentration of sulfuric acid does not exceed 25 wt.-% based on the total weight of the cellulose-containing biomass present in the treatment mixture and is preferably kept as low as possible. This becomes even more important at higher processing temperatures, because higher processing temperatures also promote the formation of undesired by-products. Thus, the higher the processing temperature, the lower the concentration of sulfuric acid should be selected. A low concentration of sulfuric acid is also preferable with respect to subsequent enzymatic saccharification, because the enzyme activity decreases if the pH is too low. Accordingly, a low concentration of sulfuric acid in the treatment mixture allows direct subjection of the treatment mixture containing the treated cellulose-containing biomass to enzymatic saccharification without removal of the aqueous acid-containing liquid phase (see also below).

In this regard, it should be considered that other acids, if present in the treatment mixture, contribute to the decrease of the pH and may further promote the formation of undesired by-products. Accordingly, the total concentration of acids is preferably kept low. In this regard it is especially preferred that in said treatment mixture the amount of methanesulfonic acid is less than 100 wt.-%, preferably 90 wt.-% or less, preferably 50 wt.-% or less and more preferably 10 wt.-% or less, based on the weight of the sulfuric acid present in the treatment mixture, and preferably the treatment mixture does not contain more than 1 wt.-% of methanesulfonic acid based on the weight of the sulfuric acid present in the treatment mixture.

The pH value of the treatment mixture is preferably in a range of from 0 to 2.5, more preferably from 0.5 to 2.0.

The treatment mixture according to the invention comprises one or more compounds of formula (I)

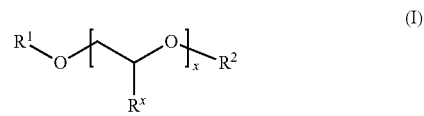

wherein in formula (I)
$R^1$ is selected from the group consisting of hydrogen and methyl
$R^2$ is selected from the group consisting of branched and non-branched alkyl having 9 to 22 carbon atoms,
each $R^x$ in any of said x groups (II)

is independently of the meaning of $R^x$ in the other groups (II) selected from the group consisting of hydrogen and methyl, x is an integer from 3 to 40.

Said compounds of formula (I) are obtainable by alkoxylation of a branched or non-branched alkanols having 9 to 22 carbon atoms with the corresponding amount of alkylene oxide selected from the group of ethylene oxide and propylene oxide (polyaddition of alkylene oxide monomers).

Within the compounds of formula (I) the groups (II)

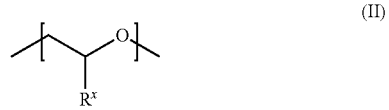

(wherein Rx is as defined above) are distributed either in a random manner, gradient manner or block-like.

Compounds of formula (I) with block-like distribution of the groups (II)

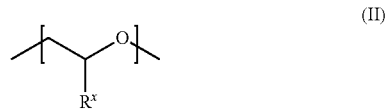

are obtainable by blockwise polyaddition of the corresponding alkylene oxide monomers.

Compounds of formula (I) with random distribution of the groups (II)

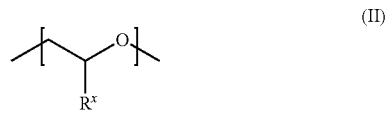

are obtainable by supplying the corresponding alkylene oxide monomers simultaneously to the reactor.

Certain preferred compounds of formula (I) are fatty alcohol ethoxylates of saturated fatty alcohols having 9 to 22 carbon atoms, preferably 10 to 18 carbon atoms, most preferably 12 to 14 carbon atoms, wherein in said ethoxylates the number of ethylene oxide units is 3 to 40, preferably 5 to 30, more preferably 7 to 15, particularly preferably 8 to 20.

Preferred are compounds of formula (I) wherein
$R^1$ is hydrogen
and/or
each $R^x$ is hydrogen
and/or
$R^2$ is selected from the group consisting of branched and non-branched alkyl having 10 to 18 carbon atoms
and/or
x is an integer from 5 to 30.

Further preferred are compounds of formula (I) wherein
$R^1$ is hydrogen
and
each $R^x$ is hydrogen
and
$R^2$ is selected from the group consisting of branched and non-branched alkyl having 10 to 18 carbon atoms
and
x is an integer from 5 to 30.

More particularly preferred are compounds of formula (I) wherein
$R^1$ is hydrogen
and
each $R^x$ is hydrogen
and
$R^2$ is selected from the group consisting of branched and non-branched alkyl having 12 to 14 carbon atoms
and
x is an integer from 5 to 30.

Particularly preferred are compounds of formula (I) wherein
(a) $R^2$ is a branched alkyl having 12 to 14 carbon atoms and x is an integer from 7 to 25
or
(b) $R^2$ is a nonbranched alkyl having 12 to 14 carbon atoms and x is an integer from 7 to 25

Especially preferred are compounds of formula (I) wherein
(a) $R^2$ is a branched alkyl having 12 to 14 carbon atoms and x is an integer from 8 to 20
or
(b) $R^2$ is a nonbranched alkyl having 12 to 14 carbon atoms and x is an integer from 8 to 20, preferably from 8 to 12.

In particularly preferred compounds of formula (I) $R^2$ is a branched alkyl having 13 carbon atoms. A C13-alcohol mixture which is suitable for the preparation of such compound of formula (I) is obtainable by the process disclosed in U.S. Pat. No. 6,963,014. Said process comprises a) bringing a butene-containing C4-hydrocarbon stream containing less than 5% by weight, based on the butene fraction, of isobutene into contact with a nickel-containing heterogeneous catalyst at elevated temperature, b) isolating a C12-olefin fraction from the reaction mixture, c) hydroformylating the C12-olefin fraction by reaction with carbon monoxide and hydrogen in the presence of a cobalt catalyst and d) hydrogenating the product from c). Said C13-alcohol mixture typically has a degree of branching in the range from 2.2 to 2.5. In order to obtain a compounds of formula (I), said C13-alcohol mixture is subjected to ethoxylation.

Due to their chemical structure, compounds of formula (I) as defined above, especially the above-defined preferred compounds of formula (I) behave as surfactants.

Preferably the one or more compounds of formula (I) as defined above are water-soluble.

Preferably the total concentration of compounds of formula (I) in said treatment mixture is in the range of from 0.05 wt.-% to 25 wt.-%, more preferably 0.1 wt.-% to 12 wt.-%, most preferably 0.5 wt.-% to 8 wt.-% in each case based on the total weight of the cellulose-containing biomass present in the treatment mixture.

At a concentration below 0.05 wt.-% based on the total weight of the cellulose-containing biomass present in the treatment mixture, the amount of compounds selected from the group consisting of compounds of formula (I) in the treatment mixture is too low so that said compounds have no significant effect on the yield of glucose in subsequent saccharification, compared to treated cellulose-containing biomass obtained by processing under identical conditions with the sole exception that the treatment mixture does not comprise any compound of formula (I). For economical reasons, the concentration of compounds selected from the group consisting of compounds of formula (I) is preferably not more than 25 wt.-% based on the total weight of the cellulose-containing biomass present in the treatment mixture. Furthermore, compounds of formula (I) behave as surfactants, and at a high concentration of surfactants foam may be formed in the treatment mixture, which is detrimental for processing the treatment mixture.

Preferably, in the treatment mixture the total amount of cellulose-containing biomass, water, sulfuric acid and compounds of formula (I) is at least 95 wt.-%, preferably at least 98 wt.-% more preferably at least 99 wt.-% based on the total weight of the treatment mixture.

Preferably the treatment mixture used in the method according to the invention is obtained by adding an aqueous treatment solution containing sulfuric acid and one or more compounds of formula (I) to said cellulose-containing biomass.

Preferably the above defined aqueous treatment solution is added to the cellulose-containing biomass in such amount that a treatment mixture is obtained comprising 3 wt.-% to 75 wt.-%, more preferably 8 wt.-% to 70 wt.-%, further preferably 15 wt.-% to 60 wt.-%, most preferably 25 wt.-% to 50 wt.-%, particularly preferably 30 wt.-% to 45 wt.-% of cellulose containing biomass, in each case based on the total weight of said treatment mixture.

Preferably, the concentration of sulfuric acid in said aqueous treatment solution is in the range of from 0.1 wt.-% to 5.5 wt.-%, preferably 0.2 wt.-% to 5.0 wt.-%, more preferably 0.3 wt.-% to 3.0 wt.-%, most preferably 0.4 wt.-% to 1.5 wt.-% in each case based on the total weight of said aqueous treatment solution.

Preferably the total concentration of compounds of formula (I) in said aqueous treatment solution is in the range of from 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-% in each case based on the total weight of said aqueous treatment solution.

Further preferably, in said aqueous treatment solution
the concentration of sulfuric acid is in the range of from 0.1 wt.-% to 5.5 wt.-%, preferably 0.2 wt.-% to 5.0 wt.-%, more preferably 0.3 wt.-% to 3.0 wt.-%, most preferably 0.4 wt.-% to 1.5 wt.-%
and
the total concentration of compounds of formula (I) in said aqueous treatment solution is in the range of from 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-%
in each case based on the total weight of said aqueous treatment solution.

Processing Conditions

In the method of the present invention said treatment mixture is subjected to a temperature in the range of from 100° C. to 220° C., wherein the pressure is selected so that at least a part of the water is in the liquid state.

When the temperature is below 100° C., the yield of glucose obtainable by saccharification of said treated cellulose-containing biomass is significantly reduced. When the temperature is above 220° C., the amount of undesirable by-products resulting from decomposition of cellulose and/or hemicellulose, like furanes, furfural and hydroxymethyl furfural, is too high. Formation of these by-products reduces the amount of cellulose available for saccharification and/or inhibits the activity of the enzymes needed for the enzymatic saccharification.

Regarding the selection of the pressure, it is important that the pressure is sufficiently high to avoid complete vaporization of the water, so as to allow interaction between the cellulose-containing biomass and the sulfuric acid dissolved in water. On the other hand, for economical and technical reasons the pressure is preferably as low as possible.

Preferably, in the method according to the present invention a temperature in the range of from 100° C. to 220° C. at a pressure in the range of from 100 kPa to 4000 kPa (wherein the pressure is selected so that at least a part of the water is in the liquid state) is maintained for a duration of not more than 120 minutes, preferably of not more than 60 minutes, further preferably of not more than 30 minutes, particularly preferably of not more than 20 minutes and most preferably of not more than 10 minutes. Thereafter the treatment mixture is allowed to cool and/or the pressure is lowered.

Preferably the temperature is in a range of 110° C. to 180° C., preferably of 120° C. to 175° C. Preferably, the pressure is in a range of 100 kPa to 1600 kPa, further preferably of 100 kPa to 1300 kPa, more preferably of 100 kPa to 1000 kPa. Further preferably, the temperature is in a range of 110° C. to 180° C., preferably 120° C. to 175° C., and the pressure is in a range of from 100 kPa to 1600 kPa, preferably 100 kPa to 1300 kPa, more preferably 100 kPa to 1000 kPa.

The skilled person is aware of the interdependence between the parameters concentration of sulfuric acid, temperature and duration of treatment. Thus, the lower the concentration of sulfuric acid the higher the temperature and/or the duration of the treatment have to be selected and vice versa (see also above). Based on his knowledge, the skilled person will select the parameters accordingly, or determine the suitable combination of said parameters by simple routine experimentation.

Especially preferred is a method of the invention wherein two or more, preferably all of the above-described preferred features regarding the processing conditions are combined.

Further preferred is a method of the invention wherein two or more, preferably all of the above-described preferred features regarding the processing conditions and the composition of the treatment mixture are combined.

In this regard especially preferred is a method according to the present invention comprising the steps of
preparing an aqueous treatment solution containing 0.4 wt.-% to 1.5 wt.-% of sulfuric acid and 0.1 wt.-% to 1 wt.-% of one or more compounds of formula (I)
adding said aqueous treatment solution to said cellulose-containing biomass so that a treatment mixture comprising said cellulose-containing biomass, water and sulfuric acid and one or more compounds of formula (I) is obtained, said treatment mixture comprising 30 wt.-% to 45 wt.-% of cellulose containing biomass, based on the total weight of said treatment mixture
subjecting said treatment mixture to a temperature in the range of from 120° C. to 175° C., wherein said temperature is maintained for a duration of not more than 40 minutes to generate a treated cellulose-containing biomass.

In the above-defined method, the one or more compounds of formula (I) are preferably selected among the above-defined preferred compounds of formula (I).

Processing Equipment

In order to allow for an efficient processing of cellulose-containing biomass according to the present invention, it is important that the solid constituents of the reaction mixture are in intimate contact with the liquid phase of the reaction mixture and—if present—steam formed by partial vaporization of the water of the mixture. This intimate contact preferably exists all the time the reaction mixture is subjected to a temperature in the range of from 100° C. to 220° C. at a pressure in the range of from 100 kPa to 4000 kPa (wherein the pressure is selected so that at least a part of the water is in the liquid state). Accordingly, for the method of the present invention, any type of reactor may be used which allows meeting this condition.

More specifically a rotating reactor, e.g. in the form of a rotating drum may be used. Alternatively, a reactor having means for mixing the reactants may be used, e.g. a stirred tank reactor. Different mixing means are applicable e.g. pug mixer, paddle mixer, ribbon mixer.

Another suitable type of reactor is a percolation reactor wherein the cellulose-containing biomass is maintained in a fixed bed, e.g. a column, a tube, a drum or a vessel, and the aqueous treatment solution comprising sulfuric acid and one or more compounds of formula (I) is flowed through the bed, e.g. a trickle-bed reactor type which allows for liquid flow involving relatively small volume of liquid. Preferably, the reactor is designed so as to allow for recirculation of the aqueous treatment solution comprising sulfuric acid and one or more compounds of formula (I).

A further suitable type of reactor is a screw-type reactor. In such type of reactor, radial mixing of solids (i.e. the cellulose-containing biomass) is provided along the length of the reactor shaft, and the aqueous treatment solution comprising sulfuric acid and one or more compounds of formula (I) is either in co-current or in counter-current flow to the solids. If present, steam formed by partial vaporization of the water of the aqueous treatment solution is a further constituent of said co-current or counter-current flow to the solids.

Combinations of above mentioned reactor types are possible, too.

The method may be operated in a discontinuous, semi-continuous or continuous operation mode.

Heating of the treatment mixture to the desired processing temperature is achieved by means of electric heating, steam or other suitable means known to those skilled in the art.

The reactor may be designed as a single step reactor so that for further processing steps like saccharification the treated cellulose-containing biomass is removed from the reactor and transferred to one or more further reactors wherein such further processing steps are carried out. Alternatively, the reactor may be designed as a multi-step reactor allowing for subsequent saccharification of the treated cellulose-containing biomass without taking the treated cellulose-containing biomass out of the reactor.

Further Processing Steps

Preferably, the method according to the present invention further comprises a step selected from the group consisting of saccharification of the treated cellulose-containing biomass so that glucose and/or other sugars are formed and optionally fermentation and/or chemical processing of the formed glucose and/or other sugars
and
further processing of the treated cellulose-containing biomass to obtain dissolving pulp.

In a first preferred alternative, saccharification of the treated cellulose-containing biomass is effected by means of enzymes (enzymatic saccharification, sometimes also referred to as enzymatic hydrolysis step). In the step of enzymatic saccharification suitable enzymes are added to the treated cellulose-containing biomass to convert the contained cellulose to glucose and/or other sugars, e.g. xylose. Suitable reactors, processing conditions and enzymes for the enzymatic saccharification are known to those skilled in the art. The enzymatic saccharification step is generally performed in stirred-tank reactors or fermentors under controlled pH, temperature, and mixing conditions. The enzymatic saccharification step may last up to 200 hours.

Enzymatic saccharification is usually carried out at temperatures from about 30° C. to about 65° C., in particular around 50° C., and at a pH in the range of from about 4 and about 6, especially around pH 5.5. To produce glucose that can be metabolized by yeast, the enzymatic saccharification is typically performed in the presence of a beta-glucosidase enzyme. Preferably an enzyme formulation comprising one or more enzymes selected from the group consisting of beta-glucosidases, exo-cellobiohydrolases, endo- and exo-glucanases, glucoside hydrolases and xylanases is used. In some cases it is preferable to use enzymes which are thermally stable and allow to the enzymatic saccharification to be carried out at temperatures from about 60° C. to about 80° C.

In a second preferred alternative, saccharification is achieved by chemical, especially thermochemical, processing of the treated cellulose-containing biomass, said chemical processing not involving enzymes. More specifically, fermentable sugars and lignin are producible from the treated cellulose-containing biomass (obtainable by the method of the present invention) by treatment with a supercritical or near-supercritical fluid or by hydrothermal treatment.

The sugars obtained by saccharification of the treated cellulose-containing biomass may serve as feedstock for obtaining a plurality of further products, either by fermentation or by chemical processing of the sugars obtained by saccharification of the treated cellulose-containing biomass.

In the fermentation step, glucose obtained by saccharification of the treated cellulose-containing biomass is fermented to ethanol by a fermenting organism, such as yeast. Suitable reactors, processing conditions and fermenting organisms for the fermentation are known to those skilled in the art. The steps of enzymatic saccharification and of fermentation are performed simultaneously in one vessel or in separate vessels. In the first alternative, the fermentation is carried out simultaneously with the enzymatic saccharification in the same vessel under controlled pH, temperature, and mixing conditions. Typical products of the fermentation of glucose include ethanol, butanol, lactic acid, butanediol, amino acids and succinic acid.

Chemical processing of sugars obtained by saccharification of the treated cellulose-containing biomass refers to processes wherein said sugars are subjected to a chemical reaction not involving fermentation to obtain other chemical products. Preferably, said chemical reaction is carried out in the presence of one or more catalysts which are not enzymes. Typical products obtainable by chemical processing of glucose include sugar alcohols, sugar acids, hydroxymethylfurfural and derivatives thereof.

In a preferred method of the present invention, the liquid phase of the treatment mixture is at least partially separated from the treated cellulose-containing biomass prior to saccharification of the treated cellulose-containing biomass, e.g. by filtration and subsequent washing of the treated cellulose-containing biomass. The liquid phase of the treatment mixture consists of an aqueous solution, which contains hemicellulosic sugars (e.g. xylose) and further water-soluble decomposition products formed in the step of subjecting the treatment mixture to a temperature in the range of from 100° C. to 220° C. at a pressure in the range of from 100 kPa to 4000 kPa. This aqueous solution may be used as a feedstock for further processes. Typical products obtainable by chemical processing of xylose include sugar alcohols, sugar acids, furfural and derivatives thereof.

Separating the liquid constituents of the treatment mixture from the treated cellulose-containing biomass prior to enzymatic saccharification has the advantage that water-soluble by-products like furanes, furfural and hydroxymethylfurfural which may act as enzyme inhibitors are removed from the treated cellulose-containing biomass which is subjected to enzymatic separation. A disadvantage of this specific method is that the compounds of formula (I) may be removed from the treated cellulose-containing biomass so that any possible positive effect (as described above) of the presence of compounds of formula (I) during enzymatic saccharification may be reduced.

In an alternative preferred method according to the present invention the enzymes for the saccharification are added to the treatment mixture comprising the treated cellulose-containing biomass without prior removal of the liquid phase from the treated cellulose-containing biomass, thus reducing complexity of the overall processing method. Furthermore, in this method the compounds of formula (I) remain in the treated cellulose-containing biomass so that the above-described positive effects may be obtained as much as possible. For this specific method of the present invention, it is especially important that the acid concentration in the treatment mixture is low and that the step of subjecting the treatment mixture to a temperature in the range of from 100° C. to 220° C. at a pressure in the range of from 100 kPa to 4000 kPa is carried out in such manner that the amount of by-products like furanes, furfural and hydroxymethylfurfural which may act as enzyme inhibitors is as small as possible. If necessary the acid in the treatment mixture is neutralized to adjust the pH to a value suitable for enzymatic saccharification.

Another field of application of the present invention is related to the production of dissolving pulp. Dissolving pulp (also called dissolving cellulose) is a bleached wood pulp or cotton linters having a high content of cellulose (>90%). It has a high level of brightness and uniform molecular-weight distribution. This pulp is manufactured for uses that require a high chemical purity, and particularly low hemicellulose content, since the hemicellulose can interfere with subsequent processes. Dissolving pulp is so named because it is not made into paper, but dissolved either in a solvent or by derivatization into a homogeneous solution, which makes it completely chemically accessible and removes any remaining fibrous structure. Once dissolved, it can be spun into textile fibers, or chemically reacted to produce derivatized celluloses, such as cellulose triacetate, a plastic-like material formed into fibers or films, or cellulose ethers such as methyl cellulose, used as a thickener. Dissolving pulp is mainly produced chemically from the pulpwood by the sulfite process or the kraft process with an acid prehydrolysis step to at remove hemicelluloses. As noted above, in the treated cellulose-containing biomass obtainable by the method of the present invention the content of hemicellulose and/or lignin is typically decreased due to decomposition to xylose. Therefore, the treated cellulose-containing biomass obtainable by the method of the present invention is suitable for further processing to obtain dissolving pulp.

Hereinbelow the invention is described further by means of examples.

EXAMPLES

1. Pretreatment of Cellulose-Containing Biomass:
An autoclave with an anchor stirrer is filled with a treatment mixture consisting of
an amount of chopped straw as specified in table 1 below, and an aqueous treatment solution comprising sulfuric acid in the concentration specified in table 1 and optionally either a compound of formula (I) (examples 7-11) or a comparison additive which is not a compound of formula (I) (examples 2-6) as specified in type and concentration in table 1.

In the above-defined treatment mixture, the weight fraction of chopped straw corresponds to 5% of the total weight of the treatment mixture, and the weight fraction of the aqueous treatment solution corresponds to 95% of the total weight of the treatment mixture.

Hereinbelow, the compounds of formula (I) and the comparison additives which are not compounds of formula (I) are commonly referred to as additives. For the chemical structure of said additives, see table 2 hereinbelow. All additives are commonly used surfactants which are commercially available. For comparison example 1 is carried out using an aqueous treatment solution comprising sulfuric acid in the concentration specified in table 1 and no additive.

For preparing the above-defined aqueous treatment solutions, an aqueous solution comprising 96 wt.-% sulfuric acid is diluted with deionized water.

The autoclave is purged three times with nitrogen gas and the treatment mixture is heated to the target temperature specified in table 1 under stirring (50 rpm). The resulting pressure is in the range of 280 kPa to 340 kPa. After reaching the target temperature, the temperature is maintained for the time interval according to table 1. Thereafter heating is turned off, the mixture is allowed to cool to ambient temperature, and then the autoclave is relaxed and is emptied. The obtained mixture comprising treated cellulose-containing biomass is filtered through a frit (pore size 2), and the weight of the liquid phase obtained as filtrate is determined, see table 1. The weight of the treated cellulose-containing biomass (solid phase) obtained as filtration residue is determined, see table 1, and then a sample of the obtained treated cellulose-containing biomass is subjected to enzymatic saccharification as described herein below.

2. Enzymatic Saccharification of Cellulose-Containing Biomass:

4.50 g of the treated cellulose-containing biomass obtained as described above are weighed into a 50 mL tube and filled up with deionized water containing 0.1 wt.-% sodium azide to a volume of 30 mL. A pH-value of 5.5 is adjusted by adding 100 mM phosphate buffer. An enzyme formulation comprising one or more enzymes selected from the group consisting of beta-glucosidases, exo-cellobiohydrolases, endo- and exo-glucanases, glucoside hydrolases and xylanases is added in the concentration as specified in table 1. The mixture is incubated in an Eppendorf-Thermomixer at 350 rpm and 53° C. (50° C. internal). At certain intervals specified in table 1, 1 mL samples are taken and diluted 1:1 with water. After centrifugation of the sample the clear supernatant is analyzed by HPLC for the concentrations of glucose and xylose.

The "yields" as indicated in table 1 are either absolute yields stated in arbitrary units or normalized absolute yields. Thus, the yields in table 1 are not based on a theoretical yield. The yields of glucose obtained after 24 hours and 48 hours of enzymatic saccharification are extrapolated to the quantity of treated cellulose-containing biomass and normalized with respect to the yield after 24 hours of enzymatic saccharification according to example No. 1 (pretreatment using an aqueous treatment solution comprising sulfuric acid and no additive).

Pretreatment and enzymatic saccharification of examples 1-11 was carried out under the same conditions with the exception of the type of additive in the treatment mixture. Surprisingly it has been found that the presence of a compound of formula (I) in the treatment mixture results in a higher yield of glucose after 24 and 48 hours of enzymatic saccharification (examples 7-11), compared to example 1 where no additive is present in the treatment mixture. On the other hand, the presence of a comparison additive (examples 2-6) in the treatment mixture instead of a compound of formula (I) results in a significantly lower increase of the yield of glucose after 24 hours (examples 4 and 5) and 48 hours (examples 3-5) of enzymatic saccharification or even in a decrease of the yield of glucose after 24 hours (examples 2, 3 and 6) and 48 hours (examples 2 and 6) of enzymatic saccharification. This finding indicates a strong influence of the chemical structure as well as the molecule size of such additives. Furthermore, the results show that not all kinds of surfactants have an advantageous effect on the yield of glucose. More specifically some kinds of surfactants even have a detrimental effect.

It is noted that in the above-described examples the concentration of cellulose-containing biomass based on the total weight of the treatment mixture is rather close to the lower limit of the above-defined preferred range of 3 wt.-% to 75 wt.-%. However it is common practice in the technical field of the present invention that the effect of an additive with respect to biomass is initially studied in the presence of a low concentration of biomass. Based on the results gained from the examples described herein, the skilled person based on his knowledge is capable of routinely scaling up the method of the present invention to higher concentrations of cellulose-containing biomass.

TABLE 1

| Example No. | 1 | 2 | 3 | 4 | 5 | 6 | 7 | 8 | 9 | 10 | 11 |
|---|---|---|---|---|---|---|---|---|---|---|---|
| Pretreatment of chopped straw to give treated cellulose-containing biomass | | | | | | | | | | | |
| Mass of chopped straw/g | 7.5 | 7.5 | 7.5 | 7.5 | 7.5 | 7.5 | 7.5 | 7.5 | 7.5 | 7.5 | 7.5 |
| Sulfuric acid conc./wt.-% of aq. treatment solution | 0.35 | 0.35 | 0.35 | 0.35 | 0.35 | 0.35 | 0.35 | 0.35 | 0.35 | 0.35 | 0.35 |
| Additive type and conc./wt.-% of aq. treatment solution | / | 0.25% Additive 1 | 0.25% Additive 2 | 0.25% Additive 3 | 0.25% Additive 4 | 0.25% Additive 5 | 0.25% Additive 6 | 0.25% Additive 7 | 0.25% Additive 8 | 0.25% Additive 9 | 0.25% Additive 10 |
| Temperature/° C. | 155 | 155 | 155 | 155 | 155 | 155 | 155 | 155 | 155 | 155 | 155 |
| Hold time at target temperature/min | 0 | 0 | 0 | 0 | 0 | 0 | 0 | 0 | 0 | 0 | 0 |
| Liquid phase (filtrate)/g | 115.9 | 115.0 | 118.4 | 117.0 | 117.2 | 116.8 | 113.2 | 119.5 | 119.6 | 120.8 | 118.7 |
| Solid phase (filtration residue)/g | 25.3 | 27.2 | 24.1 | 26.3 | 26.8 | 27.5 | 30.0 | 24.0 | 26.0 | 21.9 | 27.1 |
| Enzymatic saccharification | | | | | | | | | | | |
| Used treated cellulose-containing biomass/g | 4.50 | 4.50 | 4.50 | 4.50 | 4.50 | 4.50 | 4.50 | 4.50 | 4.50 | 4.50 | 4.50 |
| Enzyme dosage/mg Protein per g dry treated cellulose-containing biomass | 5 | 5 | 5 | 5 | 5 | 5 | 5 | 5 | 5 | 5 | 5 |
| Glucose concentration after 24 h/mg/mL | 7.70 | 5.93 | 7.82 | 7.86 | 8.37 | 3.92 | 9.83 | 14.15 | 12.26 | 15.90 | 9.04 |
| Glucose concentration after 48 h/mg/mL | 8.48 | 7.06 | 9.18 | 9.71 | 9.97 | 4.25 | 11.24 | 15.45 | 13.92 | 17.49 | 11.38 |
| Calculations | | | | | | | | | | | |
| factor cellulose-containing biomass 'treated/used in saccharification' | 5.62 | 6.04 | 5.36 | 5.84 | 5.96 | 6.11 | 6.67 | 5.33 | 5.78 | 4.87 | 6.02 |
| Extrapolated yield of glucose from treated cellulose-containing biomass/absolute | | | | | | | | | | | |
| Glucose after 24 h enzymatic saccharification/mg/mL | 43.27 | 35.86 | 41.89 | 45.96 | 49.85 | 23.94 | 65.56 | 75.47 | 70.86 | 77.38 | 54.43 |
| Glucose after 48 h enzymatic saccharification/mg/mL | 47.70 | 42.66 | 49.17 | 56.74 | 59.38 | 25.97 | 74.92 | 82.41 | 80.40 | 85.11 | 68.55 |
| Norm: Glucose after 24 h enzymatic saccharification (pretreatment without additive) | 43.27 | 43.27 | 43.27 | 43.27 | 43.27 | 43.27 | 43.27 | 43.27 | 43.27 | 43.27 | 43.27 |

TABLE 1-continued

| Example No. | 1 | 2 | 3 | 4 | 5 | 6 | 7 | 8 | 9 | 10 | 11 |
|---|---|---|---|---|---|---|---|---|---|---|---|
| Yield of glucose from treated cellulose-containing biomass/normalized | | | | | | | | | | | |
| Glucose after 24 h enzymatic saccharification | 1.00 | 0.83 | 0.97 | 1.06 | 1.15 | 0.55 | 1.52 | 1.74 | 1.64 | 1.79 | 1.26 |
| Glucose after 48 h enzymatic saccharification | 1.10 | 0.99 | 1.14 | 1.31 | 1.37 | 0.60 | 1.73 | 1.90 | 1.86 | 1.97 | 1.58 |

TABLE 2

| Additive name | Compound of formula (I) | Chemical structure |
|---|---|---|
| Additive 1 | no | Carboxymethylcellulose having 0.5 carboxy units per cellulose unit |
| Additive 2 | no | Alkyl polyglucoside based on natural plant origin $C_8$-$C_{14}$ fatty alcohols |
| Additive 3 | no | Hexyl ethoxylate with about 4 ethylene oxide units |
| Additive 4 | no | Phenyl ethoxylate with about 15 ethylene oxide units |
| Additive 5 | no | Sodium linear C10-C13 alkylbenzene sulfonate |
| Additive 6 | yes | Branched C10-alkyl ethoxylate with about 10 ethylene oxide units |
| Additive 7 | yes | Mixture of C12-C14-alkyl ethoxylates with on average 9.5 ethylene oxide units |
| Additive 8 | yes | Branched C13-alkyl ethoxylate with about 10 ethylene oxide units |
| Additive 9 | yes | Branched C13-alkyl ethoxylate with about 20 ethylene oxide units |
| Additive 10 | yes | Branched C13-alkyl ethoxylate with about 3 ethylene oxide units |

The invention claimed is:

1. A method for processing cellulose-containing biomass, comprising:

subjecting a treatment mixture comprising cellulose-containing biomass, water and sulfuric acid to a temperature in the range of from 100° C. to 220° C. at a pressure in the range of from 100 to 4000 kPa, wherein the pressure is selected so that at least a part of the water is in the liquid state, to generate a treated cellulose-containing biomass, wherein said treatment mixture further comprises one or more compounds of formula (I)

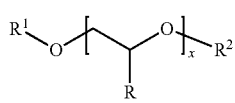

(I)

wherein in the formula (I) each x group is formula (II), $R^1$ is selected from the group consisting of hydrogen and methyl, $R^2$ is selected from the group consisting of branched and non-branched alkyl having 9 to 22 carbon atoms, R is independently selected from the group consisting of hydrogen and methyl

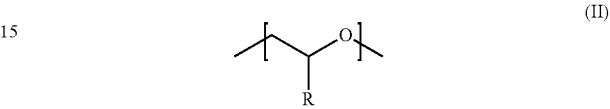

(II)

and x is an integer from 3 to 40.

2. The method according to claim 1, wherein a concentration of the sulfuric acid in the treatment mixture is in a range of from 0.1 wt. % to 25 wt. %, based on the total weight of the cellulose-containing biomass present in the treatment mixture.

3. The method according to claim 1, wherein in said treatment mixture an amount of methanesulfonic acid is less than 100 wt. %, based on the weight of the sulfuric acid present in the treatment mixture.

4. The method according to claim 1, wherein in one or more of said compounds of formula (I)

$R^1$ is hydrogen, each R is hydrogen, $R^2$ is selected from the group consisting of branched and non-branched alkyl having 10 to 18 carbon atoms, and x is an integer from 5 to 30.

5. The method according to claim 1, wherein in one or more of said compounds of formula (I)

(a) $R^2$ is a branched alkyl having 12 to 14 carbon atoms and x is an integer from 7 to 25 or (b) $R^2$ is a nonbranched alkyl having 12 to 14 carbon atoms and x is an integer from 7 to 25.

6. The method according to claim 1, wherein said cellulose-containing biomass is selected from the group consisting of plant biomass, agricultural wastes, forestry residues, sugar processing residues, paper waste and blends thereof.

7. The method according to claim 1, wherein the temperature in the range of from 100° C. to 220° C. at a pressure in the range of from 100 kPa to 4000 kPa wherein the pressure is selected so that at least a part of the water is in the liquid state is maintained for a duration of not more than 120 minutes.

8. The method according to claim 1, wherein the temperature is in a range of 110° C. to 180° C.

9. The method according to claim 1, wherein the pressure is in a range of from 100 kPa to 1600 kPa.

10. The method according to claim 1, wherein said treatment mixture comprises 3 wt.-% to 75 wt. of cellulose-containing biomass, based on the total weight of said treatment mixture.

11. The method according to claim 1, wherein said treatment mixture is obtained by adding an aqueous treatment solution containing sulfuric acid and one or more compounds of formula (I) to said cellulose-containing biomass.

12. The method according to claim 11, wherein in said aqueous treatment solution:
the concentration of sulfuric acid is in the range of from 0.1 wt. % to 5.5 wt. %,
and/or
the total concentration of compounds of formula (I) is in the range of from 0.01 wt. % to 5 wt. %,
in each case based on the total weight of said aqueous treatment solution.

13. The method according to claim 1, wherein in the treatment mixture the total amount of cellulose-containing biomass, water, sulfuric acid and compounds of formula (I) is at least 95 wt. %, based on the total weight of the treatment mixture.

14. The method according to claim 1, further comprising (a) and/or (b):
(a) saccharification of the treated cellulose-containing biomass so that glucose and/or other sugars are formed, and optionally fermentation and/or chemical processing of the formed glucose and/or other sugars, and/or
(b) further processing of the treated cellulose-containing biomass to obtain dissolving pulp.

15. The method according to claim 1, wherein in one or more of said compounds of formula (I)
$R^1$ is hydrogen,
each R is hydrogen,
$R^2$ is selected from the group consisting of branched and non-branched alkyl having 10 to 14 carbon atoms, and
x is an integer from 3 to 20.

16. The method according to claim 1, wherein in one or more of said compounds of formula (I), $R^2$ is a branched alkyl having 10 to 13 carbon atoms and x is an integer from 3 to 20; or $R^2$ is a non-branched alkyl having 12 to 14 carbon atoms and x is an integer from 8 to 20.

17. The method according to claim 16, wherein in one or more of said compounds of formula (I), $R^2$ is a branched alkyl having 10 to 13 carbon atoms and x is an integer from 3 to 20.

18. The method according to claim 16, wherein in one or more of said compounds of formula (I), $R^2$ is a non-branched alkyl having 12 to 14 carbon atoms and x is an integer from 8 to 20.

* * * * *

UNITED STATES PATENT AND TRADEMARK OFFICE
CERTIFICATE OF CORRECTION

PATENT NO. : 10,337,144 B2  
APPLICATION NO. : 15/552522  
DATED : July 2, 2019  
INVENTOR(S) : Frank Rittig et al.

Page 1 of 1

It is certified that error appears in the above-identified patent and that said Letters Patent is hereby corrected as shown below:

In the Specification

In Column 5, Line 18, "Rx" should read -- $R^x$ --, therefor.

In the Claims

In Column 15, Line 67, Claim 1, "methyl" should read -- methyl, --, therefor.

In Column 16, Line 60, Claim 10, "3 wt.-% to 75 wt." should read -- 3 wt. % to 75 wt. % --.

Signed and Sealed this  
Thirty-first Day of December, 2019

Andrei Iancu  
*Director of the United States Patent and Trademark Office*